United States Patent [19]

Dahan

[11] Patent Number: 4,571,177
[45] Date of Patent: Feb. 18, 1986

[54] ORTHODONTIC JACK FOR MAXILLARY EXPANSION APPLIANCE

[75] Inventor: José Dahan, Kraainem, Belgium

[73] Assignee: Rodam SA, Geneve, Switzerland

[21] Appl. No.: 697,732

[22] Filed: Feb. 4, 1985

[30] Foreign Application Priority Data

Feb. 13, 1984 [CH] Switzerland .............................. 681/84

[51] Int. Cl.³ ............................................... A61C 7/00
[52] U.S. Cl. ......................................................... 433/7
[58] Field of Search .............................................. 433/7

[56] References Cited
U.S. PATENT DOCUMENTS

| | | | |
|---|---|---|---|
| 3,835,540 | 9/1974 | Biederman | 433/7 |
| 4,144,643 | 3/1979 | Krygier | 433/7 |
| 4,197,644 | 4/1980 | Ackerman | 433/7 |

Primary Examiner—Robert Peshock
Attorney, Agent, or Firm—Parkhurst & Oliff

[57] ABSTRACT

Each of two nuts includes two cylindrical recesses, the bottoms of which are pierced by openings of smaller diameter. Each of two jack bodies comprises, besides one of the nuts, two independent rods, the rectilinear ends of which are each fitted in one of the recesses and each include a blind hole serving as a guide for one of two guide pins connecting the nuts. By means of a screw having oppositely threaded ends screwed into tapped bores in the nuts, the jack bodies can be moved toward or away from one another, whereby forces situated strictly in the same plane can be exerted upon devices anchoring the appliance to the teeth. These anchoring devices are independent of one another and are each connected to only one tooth.

5 Claims, 3 Drawing Figures

ORTHODONTIC JACK FOR MAXILLARY EXPANSION APPLIANCE

This invention relates to orthodontic appliances, and more particularly to an orthodontic screw-jack for an appliance for expanding the dental arches, of the type comprising two jack bodies and, between them, connecting means comprising sliding guide elements and a screw capable of adjusting the spacing between the jack bodies, each jack body comprising a nut to which two rods connecting the nut to anchoring devices are fixed, and each of the rods of each jack body including a rectilinear extremity fitted in the nut along an axis parallel to the axis of the screw.

Jacks of this type have already been proposed, particularly in U.S. Pat. Nos. 3,835,540 and 4,197,644. In these prior art screw-jacks, the two rods of each jack body can be fixed at their ends remote from the jacks to one or more anchoring devices capable of bearing against one or more teeth in order to exert upon them the desired corrective effect. The two rods connected to the same nut may also form the two ends of a single segment of wire, the central segment of which is given a U-shape and receives the anchoring device or devices provided for.

The design of such screw-jacks must permit making them small enough to be applicable to any maxillary. Moreover, it is advantageous for them to be of simple construction, for there to be no production difficulties in obtaining adequate guiding precision and adjustment of the spacing between the jack bodies, and for the orthodontic appliance to be easy to put in place. Yet the prior art jacks of the aforementioned type do not make it possible to achieve these various objectives to a satisfactory extent.

It is therefore an object of this invention to provide an improved orthodontic screw-jack for a maxillary expansion appliance which remedies this shortcoming.

To this end, in the orthodontic screw-jack according to the present invention, of the type initially mentioned, each of the extremities of the rods is fitted in a recess having a bottom pierced by an opening, and the connecting means further comprise two rectilinear pins slidingly fitted into these openings and into blind holes in the extremities of the rods.

A preferred embodiment of the invention will now be described in detail with reference to the accompanying drawings, in which.

Figure 1:
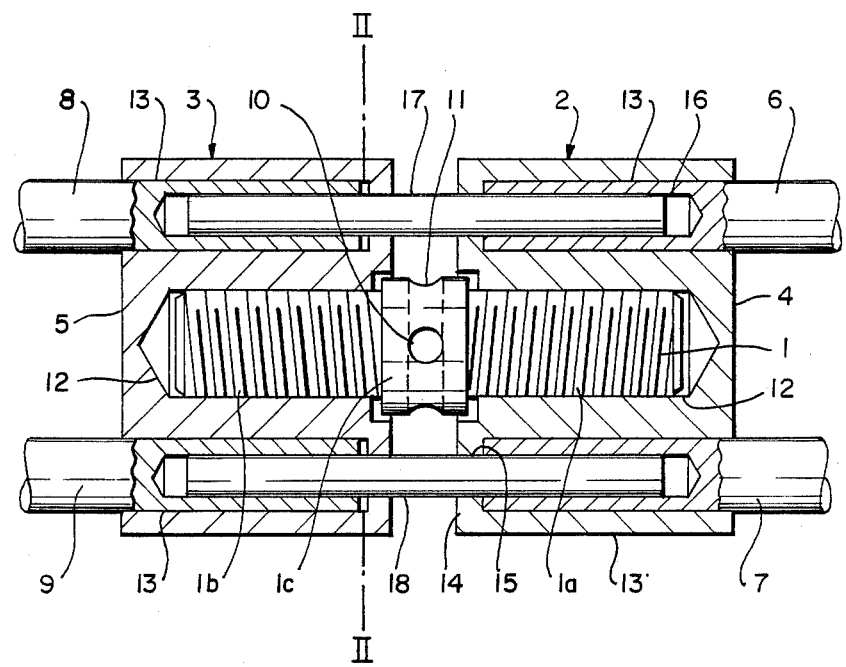
FIG. 1 is a sectional view in a plane containing the axis of the screw.
Figure 2:
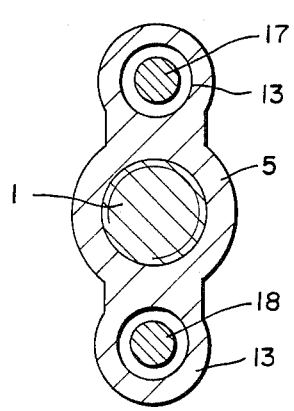
FIG. 2 is a section taken on the line II—II of FIG. 1.

The screw-jack shown in the drawing is composed essentially of a screw 1 and two jack bodies 2 and 3, each comprising a nut 4, 5 and two connecting rods, viz., rods 6, 7 for jack body 2 and rods 8, 9 for jack body 3. All these elements are made of a metal which is stable, resistant to chemical attack, and compatible with use in appliances for the correction of dental irregularities. Each nut 4, 5 is in the shape of a flat piece of generally rectangular outline, the width of which may be on the order of 10 mm and the thickness on the order of 4 mm.

Screw 1 includes two threaded portions 1a and 1b connected by a central core 1c of slightly larger diameter provided with two holes 10 and 11 intersecting it diametrically at right angles.

Each nut 4 or 5 includes along its central longitudinal axis a tapped bore 12 adapted to receive one of the two threaded portions 1a, 1b of screw 1, these portions having right-hand and left-hand threads, respectively, so that rotation in one direction causes nuts 4 and 5 to move toward one another, while rotation in the opposite direction causes them to move apart.

On either side of tapped bore 12, each of the nuts 4 and 5 includes two cylindrical recesses 13 having axes parallel to that of bore 12 and disposed in symmetrical positions with respect to bore 12. Each recess 13 extends from the end face of the nut remote from core 1c of screw 1 almost to the other end face, i.e., that nearest core 1c. Hence each recess 13 includes a thin bottom 14 which is seen to be pierced by a circular opening 15 smaller than the diameter of recess 13. This latter diameter is adapted to that of rods 6, 7, 8, and 9, for at the ends of these rods facing nuts 4 and 5 there are rectilinear portions, each fitted into one of the recesses 13. Furthermore, these ends of the rods each include a blind hole 16 of the same diameter as openings 15 in the bottoms 14 of recesses 13, or of a matching diameter.

Figure 3:
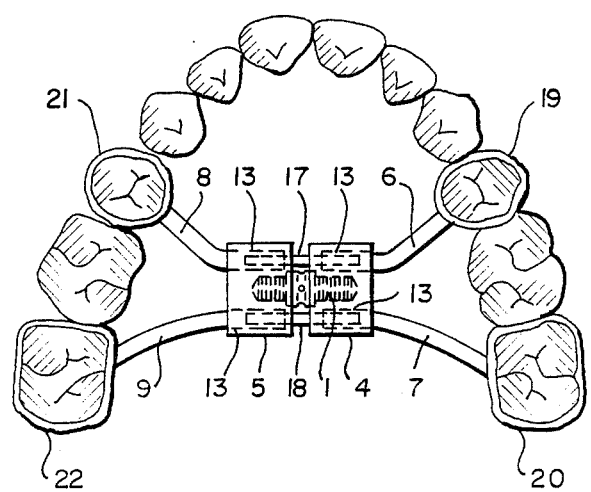
FIG. 3 is a plan view on a smaller scale showing an expansion appliance equipped with the jack of FIGS. 1 and 2.

The jack bodies are connected, and are kept in parallel positions and prevented from rotating when the screw is turned, by means of two cylindrical guide pins 17 and 18 of dimensions such that they can fit in blind holes 16 through openings 15. All the adjustments will be carried out in such a way as to allow smooth sliding, but without any play between the respective parts. As the appliance described is intended to work expandingly, the end faces of rods 6, 7, 8, and 9 can bear against the bottoms 14 in nuts 4 and 5 so as to tranmit the force of the jack to the anchoring devices. This is illustrated in FIG. 3, which shows how each of the rods 6, 7, 8, and 9 is connected independently to an anchoring device 19, 20, 21, or 22, each of the latter devices being connected independently to a tooth. Thus, guide pins 17 and 18 ensure that the two jack bodies are maintained in parallel positions, allowing expansion of the appliance against the resisting force of the dental arches by manipulating screw 1. As guide pins 17 and 18 are coaxial with the ends of rods 6, 7, 8, and 9 which transmit the resisting forces, any moments of torsion which may be due to buckling stresses exerted on the jack are reduced to a minimum. At the same time, the jack likewise takes up a minimum amount of space with the arrangement described above.

It is, in fact, extremely difficult to place such a jack in a position close to the palate when the patient's maxillary is very small. The compact size of the jack described above, however, by freeing the space of the maxillary cavity for the tongue, makes it possible to overcome this difficulty. It allows the patient to articulate correctly without losing any of its efficiency in transmitting the rotary force.

Recesses 13 in nuts 4, 5 might be other than cylindrical in shape: they might, for instance, be polygonal, i.e., square or triangular, in cross-section, rods 6, 7, 8, and 9 then having the same shape. In this case, each rod would be made integral with the corresponding screw not only in direction but also with respect to rotation about the axis of the recess.

What is claimed is:

1. An orthodontic screw-jack for a maxillary expansion appliance having anchoring means, of the type having two spaced jack bodies, connecting means disposed between said jack bodies and including sliding guide elements and a screw for adjusting the spacing between said jack bodies, each of said jack bodies including a nut and two rods fixed to said nut for connecting said nut to said anchoring means and each including a rectilinear extremity fitted in said nut along an axis parallel to the axis of said screw, wherein the improvement comprises:

two recesses situated in each said nut for respectively receiving a said rectilinear extremity of one of said rods, each of said recesses including a bottom pierced by an opening, a blind hole situated in each said rectilinear extremity, and two rectilinear pins forming part of said connecting means and each slidingly fitted at each end in a respective said opening and in a respective said blind hole.

2. The screw-jack of claim 1, wherein said rods are independent of one another and each bear at the end thereof remote from said rectilinear extremity a separate said anchoring means.

3. The screw-jack of claim 1, wherein said recesses have a cylindrical inner face.

4. The screw-jack of claim 3, wherein said blind holes and the associated said recesses are coaxial.

5. The screw-jack of claim 1, wherein said recesses are polygonal in cross-section.

* * * * *